United States Patent [19]

Nussenblatt et al.

[11] Patent Number: 5,294,604
[45] Date of Patent: Mar. 15, 1994

[54] METHOD OF TREATING OCULAR DISEASES BY PERIOCULAR ADMINISTRATION OF CYCLOSPORINE A OR G

[75] Inventors: Robert B. Nussenblatt, Bethesda; Alan G. Palestine, Potomac, both of Md.

[73] Assignee: The Government of the United States of America as represented by the Secretary of the Department of Health and Human Services, Washington, D.C.

[21] Appl. No.: 453,793

[22] Filed: Dec. 20, 1989

[51] Int. Cl.$^5$ .................. A61K 37/02; C07K 7/06; C07K 5/12
[52] U.S. Cl. .......................... 514/11; 514/9; 514/15
[58] Field of Search ................. 514/11, 15, 9

[56] References Cited

U.S. PATENT DOCUMENTS 4,649,047  3/1987  Kaswan ........................... 514/912
4,839,342  6/1989  Kaswan ............................. 514/11

OTHER PUBLICATIONS

Nussenblatt et al, "Immunohistologic Findings and . . . ," *Amer. J. of Ophthalmology*, 107:160–166, Feb. 1989.
Nussenblatt et al, "A Comparison of the Effectiveness . . . ," *J. of Immunopharmacology*, 8(3), (1986), pp. 427–435.

Primary Examiner—Merrell C. Cashion, Jr.
Assistant Examiner—S. G. Marshall
Attorney, Agent, or Firm—Birch, Stewart, Kolasch & Birch

[57] ABSTRACT

The present invention provides a method of treating ocular diseases by the administration of cyclosporine A or G by periocular injection in a pharmaceutically acceptable carrier.

16 Claims, No Drawings

METHOD OF TREATING OCULAR DISEASES BY PERIOCULAR ADMINISTRATION OF CYCLOSPORINE A OR G

BACKGROUND OF THE INVENTION

1. Field of the Invention

The present invention relates to a method for treating ocular disease and, more specifically, to a method for treating ocular disease by administration of cyclosporine A or G to a patient through a periocular injection pharmaceutically acceptable carrier to a patient.

2. Description of Related Art

Cyclosporines A and G belong to a class of structurally distinct, cyclic, poly-N-methylated undecapeptides having valuable pharmacological, in particular immunosuppressive, anti-inflammatory and anti-protozoal activity. The first to be isolated and the "parent" compound of this class is the naturally occurring fungal metabolite "cyclosporine," also known as cyclosporine A, the production and properties of which are described for example in U.S. Pat. No. 4,117,118. Note that use of the term "cyclosporin(e)" alone is generally recognized in the art to refer only to cyclosporine A unless otherwise stated. Since the original discovery of cyclosporine A, a wide variety of a naturally occurring cyclosporines have been isolated and identified and many further non-natural cyclosporines have been prepared by synthetic or semisynthetic means or by the application of modified cultured techniques. The class comprised by the cyclosporines is thus now substantial and includes, for example, the naturally occurring cyclosporines A, C, D and G, as well as various semisynthetic derivatives thereof, such as their dihydroderivatives, as disclosed, e.g., in U.S. Pat. Nos. 4,108,985; 4,210,581 and 4,220,641, and other natural and artificial cyclosporines such as those disclosed in European Patent Publication No. 0058,134 B1.

Cyclosporine A has been used in the treatment of ocular disease mediated by immune processes. Lately, cyclosporine A has been used locally in the form of ophthalmic drops for the treatment of disorders involving the anterior portion of the eye and conjunctiva with good results as reported at Holland et al, ("Immunohistologic Findings and Results of Treatment With Cyclosporine in Ligneous Conjunctivitis," *Amer. J. of Ophthalmology*, 107:160–166, Feb. 1989). Cyclosporin A has also been used in an ophthalmic treatment by topical administration thereof to the eye (U.S. Pat. No. 4,649,047 to Kaswan), as well as for increasing tear production by topical administration thereof (U.S. Pat. No. 4,839,342 to Kaswan).

A concern with cyclosporine A has been its potential to cause nephrotoxicity. Systemic therapy with cyclosporine A has been associated with renal toxicity (kidney failure) and increased incidence of opportunistic infections. The systemic side effects of cyclosporine A are so severe that they sometimes limit its use to life-threatening or severe sight-threatening diseases. Topical application of this drug can lead to systemic absorption with measurable plasma levels if given often enough for severe local inflammatory conditions, such as corneal graft rejection. In individuals such as newborns, those with renal disease, or those taking non-steroidal anti-inflammatory agents, this has the increased potential to limit the usefulness of cyclosporine A.

As an alternative agent for treating ocular diseases, cyclosporine G has been evaluated in an ocular inflammatory model and it is found to be at least 80% as effective as cyclosporine A at equivalent intracameral dosages as reported by Nussenblatt et al ("A Comparison of the Effectiveness of Cyclosporine A, D and G in the Treatment of Experimental Autoimmune Uveitis in Rats," *J. of Immunopharmacology*, 8(3), (1986), pp. 427–435). Cyclosporin G differs from cyclosporine A in that the L-nor-valine has replaced alpha-amino butyric acid at the amino acid 2 position. Cyclosporine G has a molecular weight of 1217, as compared to cyclosporine A with a molecular weight of 1203. Cyclosporine G has also been found not to be as nephrotoxic as cyclosporine A as reported by Calne et al ("Cyclosporin G: Immunosuppressive Effect in Dogs with Renal Allografts," Lancet ii:1342, 1985). However, previous reported results have indicated that topical administration of cyclosporine G does not prevent the expression of experimental autoimmune uveitis, Nussenblatt et al ((1986, pp. 427–435).

Accordingly, there exists a strong need for developing a local ocular therapeutic route which eliminates the undesirable physiological problems associated with the cyclosporine A treatment of ocular diseases, while maintaining the advantageous therapeutic properties of this treatment.

Applicants have now surprisingly discovered that administration of cyclosporine A or G by periocular injection may be used to treat ocular diseases including serious intraocular inflammatory processes requiring immunosuppression for a sustained period; and further that periocular administration of cyclosporine G to a patient may be used to effectively treat ocular diseases including endogenous uveitis, Behcet's Disease, corneal transplantation, vernal keratoconjunctivitis, ligneous keratoconjunctivitis, dry eye syndrome, anterior uveitis and onchocerciasis.

SUMMARY OF THE INVENTION

Accordingly, it is an object of this invention to provide a method for the treatment of various ocular diseases.

It is another object of the present invention to provide a method for effectively treating ocular diseases while lowering the risks of undesirable physiological problems, such as nephrotoxicity, associated with conventional treatments, such as those using cyclosporine A.

It is still another object of the present invention to provide a method for the treatment of ocular diseases by administration of cyclosporine A or G through periocular injection into the patient.

It is a further object of the present invention to provide an effective method for the treatment of ocular diseases including endogenous uveitis, Behcet's Disease, corneal transplantation, vernal keratoconjunctivitis, ligneous keratoconjunctivitis, dry eye syndrome, anterior uveitis and onchocerciasis.

Applicants have discovered that these objects of the present invention are surprising satisfied by administration of cyclosporine A or G through periocular injection thereof in a pharmaceutically acceptable carrier in order to effectively treat ocular diseases with advantageously reduced concern of the undesirable physiological effects associated with previous treatments.

DESCRIPTION OF THE PREFERRED EMBODIMENTS

The present invention provides a method for the treatment of ocular diseases by administration of cyclosporine A or G to a patient through periocular injection in a pharmaceutically acceptable carrier. Other features of the invention will become apparent in the course of the following description of exemplary embodiments which are given for purposes of illustration of the invention and are not intended to be limiting thereof.

In the case of periocular administration of cyclosporine A (CsA) or cyclosporine G (CsG) to a patient, the term "periocular" is intended to encompass, but is not limited to, subconjunctival, trans-septal, and retrobulbar injections so as to provide for a local ocular therapeutic route through the sclera, i.e. the outer coat of the eye. Use of a periocular injection is advantageous since the sclera has different absorption characteristics than does the cornea, therefore permitting higher concentrations of the administered drug to enter into the middle and back portions of the eye, the frequent site of severe inflammation. The topical application of cyclosporine (onto the cornea) may not permit penetration of large enough quantities to have a beneficial effect on intraocular inflammation. Unlike eye drops, periocular administration requires the use of a needle and should be administered by a physician experienced in such injections. It is noted that administration by periocular injection compares favorably to intracameral injection since periocular injections may be administered more frequently with a lower risk of injury to the eyeball. Preparations useful for periocular injection of CsA or CsG preferably include a dosage of the active ingredient CsA or CsG in an appropriate concentration range in solution. Preferable concentration ranges include from about 10 to 100 mg/ml, and most preferably from about 50 to 100 mg/ml. Preferable dosage ranges include from about 50 to 200 mg. Appropriate medically suitable vehicles in which CsA or CsG may be dissolved in the periocular injection preparations include but are not limited to liposomes, water suspensions and other suitable vehicles for lipophilic substances.

As a means of demonstrating the improved ocular absorption expected by administration using periocular injection, in vitro studies concerning the passage of CsA through the sclera of the eye were performed in Example 1 below.

EXAMPLE 1

In vitro studies concerning the passage of CsA through the sclera were performed using an enucleated rabbit eye, from an animal being sacrificed for studies not related to the eye. The optic nerve of the rabbit eye was tightly enclosed with a 7-0 vicryl suture in order to prevent uncontrolled absorption of the CsA into the vitreous body of the eye via the optic nerve and its vessels. Two 7-0 vicryl scleral support sutures were then placed to hold the eye in position, i.e. so that the anterior portion of the globe was facing upward. An incision was made at the pars plana and a circular cut was made all the way around the globe. The anterior segment of the eye was carefully removed from the posterior segment. The lens and a portion of the vitreous followed the anterior segment elements. The remaining posterior vitreous was removed using a battery run vitrector instrument. No attempt was made to remove the vitreous adherent to the retina. The empty vitreal cavity was then filled with RPMI 1640 solution for the purpose of keeping the retina and other layers moist and alive. The globe was then lowered into a dish containing a known amount of CsA in solution and aliquots of the intra-vitreal solution were taken on a regular basis for inspection. These aliquots were then analyzed for the presence of CsA using a radioimmune assay kit. The results of the observed scleral absorption rates of CsA are indicated in Table 1 below.

TABLE 1

| Cyclosporine A Concentration | Scleral Absorption of Cyclosporine A | | | | | | | | |
|---|---|---|---|---|---|---|---|---|---|
| | Time After Exposure (Minutes) | | | | | | | | |
| | 0 | 1 | 2 | 5 | 10 | 15 | 20 | 30 | 60 |
| RAT | | | | | | | | | |
| 2 mg/ml | 0 | — | — | — | 15* | — | 57 | — | — |
| 20 mg/ml | 0 | — | — | — | 25 | — | 32 | — | — |
| RABBIT | | | | | | | | | |
| 2 mg/ml | — | 0 | 0 | 0 | 0 | — | 31 | 400 | 217 |
| 20 mg/ml | — | 60 | 133 | 69 | 145 | 73 | — | 225 | 104 |

*cyclosporine A concentration in ng/ml

Absorption levels of CsG are expected to be very similar to those exhibited above for CsA in view of the similar pharmacokinetic properties exhibited by each of these peptides.

As further evidence that the above-noted absorption levels in Table 1 are acceptable for therapeutic treatment using CsA or CsG administered by periocular injection, studies were conducted to measure the absorption levels and therapeutic effectiveness of CsG and CsA after systemic and topical administration as described in Examples 2 and 3 below.

EXAMPLE 2

In order to assess the therapeutic effect exhibited by CsA, the following tests were conducted using the cyclosporine treatment schedule described below.

In vivo and in vitro Treatment Schedules

In vivo testing was performed on animals treated with:
(1) daily injections of CsA or CsG starting on day zero for 14 days
(2) daily injections of CsA or CsG starting on day zero for 28 days
(3) 1% topical CsG in a liposomal preparation applied for 14 days
(4) intracameral CsG administered on day 10 after S-antigen priming In vitro testing was performed using:
(1) S-antigen specific long term cell lines capable of inducing experimental autoimmune uveitis (EAU), wherein the S-antigen was prepared using the method as described by Dore et al ("A Simple and Rapid Method for Isolation of Retinal S-antigen," *Ophthalmic Res.*, 14:249, 1982). The in vitro testing was evaluated by measuring the CsA and CsG capacity to inhibit cell proliferation and interleukin-2.

Methods 200 gram female Lewis rats were immunized with 30 ug of bovine S-antigen in complete Freund's adjuvant. On day 11 following immunization, each animal received an intravitreal injection of the cyclosporine drug in one eye and received olive oil in the other eye using a 30 gauge needle inserted posterior to the ciliary body. A dose response study using 500 ng, 100 ng, 50 ng and 10 ng of CsA and 500 ng, 100 ng and 50 ng of CsG in 25 to 50 μL of olive oil was performed. Animals were killed on day 14 (or day 28) and the eyes were fixed in 10% buffered formalin, sectioned, stained and examined for EAU.

Results

1. By using a standardized histologic grading system (Nussenblatt et al, "Local Cyclosporine Therapy for Experimental Autoimmune Uveitis in Rats," *Arch. Ophthamol.*, Vol. 103, Oct. 1985, pp. 1559-1562), a masked observer found that at equivalent dosages, CsG was 80% as effective as CsA.
2. Animals treated with CsA or CsG for 14 days manifested a "rebound" and expressed severe ocular disease.
3. The minority of animals treated for 28 days did not show evidence of EAU after 60 days.

Intravitreal CsA or CsG administrated once on day 11 after immunization with S-antigen prevented the development of EAU in the treated eye only at doses of 500 ng (see Table 2 below). The untreated control eyes did develop EAU. Assuming that the volume of a rat eye is 500 μL and that the lens has a volume of 100 μL, the peak intraocular concentration of drug was approximately 1.25 μg/ml.

TABLE 2

| The Local Effect of Intravitreal CsA and CsG on EAU | | |
|---|---|---|
| Amount of Drug | Treated Eyes # Normal/Total | Untreated # Normal/Total |
| 500 ng CsA | 3/4 | 0/4 |
| 100 ng CsA | 0/4 | 0/4 |
| 50 ng CsA | 0/3 | 0/3 |
| 10 ng CsA | 0/6 | 0/3 |
| 500 ng CsG | 4/7 | 1/7 |
| 100 ng CsG | 0/6 | 0/6 |
| 50 ng CsG | 0/6 | 0/6 |

As is evident from the above test results regarding the local therapeutic effect of intravitreal CsA and CsG on EAU, effective prevention of EAU results if the administered dose approaches the amount of 500 ng. Thus, the scleral absorption measurements of CsA indicated in Table 1 in Example 1 above which correspond to periocular administration compare favorably with the effective therapeutic dosages of CsA and CsG indicated in Table 2.

EXAMPLE 3

Tests were also conducted to assess the topical absorption properties of CsA. Intraocular penetration of CsA in an olive oil vehicle was measured using the following methods:

Female Lewis rats, each 6 weeks of age and weighing approximately 200 g, were used for this series of experiments. Animals receiving topical and systemic medications were immunized in both hind foot pads and with a total of 50 μg of bovine S-antigen, prepared as described elsewhere (Wacker et al, "Experimental allergic uveitis: Isolation, characterization and localization of a soluble uveithopathogenic antigen from bovine retina," *J. Immunol.* 1982, 102, pp. 2360-2367), mixed with an equal portion of complete Freund's adjuvant augmented with H37 Mycobacterium tuberculosis to a concentration of 2.5 mg/mL. Animals receiving intracameral cyclosporine therapy were immunized with 30 μg of bovine S antigen prepared and mixed in the same fashion as above.

Topical Therapy. A 2% cyclosporine A solution in olive oil was the stock solution. Lower concentrations of the drug were obtained by diluting the stock solution with olive oil. Animals were treated topically with 2% and 0.2% cyclosporine A. For the determination of cyclosporine A penetration into the eye, only one drop (50 μL) of the concentrations tested was placed onto the eye.

Intracameral Administration. Using the stock 2% cyclosporine solution, 40 μL (800 μg) was injected intravitreally 11 days after S-antigen immunization. Other rats received intravitreal olive oil. This was performed using the operating room microscope for visualization and a 30 gauge needle.

Table 3 below illustrates the small amount of CsA in the vitreous after topical application.

TABLE 3

| Rat Vitreous Cyclosporine Levels After Local Administration | | | | | | |
|---|---|---|---|---|---|---|
| Cyclosporine Administration | Dosage | Cyclosporine Levels in Vitreous After Application,* mg/mL | | | | |
| | | 1 hr | 4 hr | 24 hr | 48 hr | 98 hr |
| Topical | 2% solution | 18 | 7 | 19 | 7 | ... |
| | 0.2% solution | 3 | 3 | 3 | 3 | ... |
| Intravitreal | 800 ug | ND | 580 | 390 | ND | 160 |
| | 80 ug | ND | 60 | 80 | ND | 30 |

*Mean of at least four eyes per group.
ND indicates not done.

The topical application of one drop of cyclosporine at two concentrations led to levels in the intraocular contents of those eyes that were extremely low, indeed at the level approaching the sensitivity of the radioimmunoassay. Somewhat higher concentrations were noted when one drop of the 20 mg/Ml (2%) solution was used as opposed to the 2 mg/mL (0.2%) preparation.

As is evident from the results in Example 3, the intraocular penetration measurements of CsA did not provide intraocular levels of the drug as high as the absorption levels indicated for Examples 1 or 2 above. Topical administration of CsG is expected to reach similar intraocular levels because of its similar pharmacokinetic properties.

It is generally preferred that the periocular administration of CsA or CsG to the patient be used in the therapeutic treatment of ocular diseases including endogenous uveitis, corneal transplantation, vernal keratoconjunctivitis, ligneous keratoconjunctivitis, dry eye syndrome, anterior uveitis and onchocerciasis.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A method for treating ocular disease which comprises administering to a patient by periocular injection cyclosporine G in a pharmaceutically acceptable carrier in an amount effective for treating ocular disease.

2. A method for treating ocular disease which comprises administering to a patient by periocular injection cyclosporine A in a pharmaceutically acceptable carrier in an amount effective for treating ocular disease.

3. A method for treating ocular disease which comprises administering to a patient by periocular injection cyclosporine G in a pharmaceutically acceptable carrier, wherein the cyclosporine G is administered in an amount of from 10 to 100 mg/ml in a medically suitable vehicle.

4. The method of claim 3, wherein the ocular disease which is treated is selected from the group consisting of endogenous uveitis, Behcet's Disease, corneal transplantation, vernal keratoconjunctivitis, ligneous keratoconjunctivitis, dry eye syndrome, anterior uveitis and onchocerciasis.

5. A method for treating ocular disease which comprises administering to a patient by periocular injection cyclosporine A in a pharmaceutically acceptable carrier, wherein the cyclosporine A is administered in an amount of from 10 to 100 mg/ml in a medically suitable vehicle.

6. The method of claim 5, wherein the ocular disease which is treated is selected from the group consisting of endogenous uveitis, Behcet's Disease, corneal transplantation, vernal keratoconjunctivitis, ligneous keratoconjunctivitis, dry eye syndrome, anterior uveitis and onchocerciasis.

7. The method of claim 3, wherein the cyclosporine G is administered in an amount of from 50 to 100 mg/ml in a medically suitable vehicle.

8. The method of claim 5, wherein the cyclosporine A is administered in an amount of from 50 to 100 mg/ml in a medically suitable vehicle.

9. The method of claim 3, wherein the dosage range is from about 50 to 200 mg.

10. The method of claim 5, wherein the dosage range is from about 50 to 200 mg.

11. The method of claim 3, wherein the medically suitable vehicle is liposomes or water suspensions.

12. The method of claim 5, wherein the medically suitable vehicle is liposomes or water suspensions.

13. A pharmaceutical composition for treating ocular disease which comprises cyclosporine G or A and a pharmaceutical carrier suitable for periocular injection.

14. The pharmaceutical composition of claim 13, wherein said cyclosporine is cyclosporine G.

15. The pharmaceutical composition of claim 13, wherein said cyclosporine is cyclosporine A.

16. The pharmaceutical composition of claim 13, wherein said pharmaceutical carrier is liposomes or a water suspension.

* * * * *